(12) United States Patent
Jiang

(10) Patent No.: US 11,890,445 B2
(45) Date of Patent: Feb. 6, 2024

(54) UNIVERSAL DISINFECTION CAP

(71) Applicant: Becton, Dickinson and Company, Franklin Lakes, NJ (US)

(72) Inventor: Chang Jiang, Butler, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 504 days.

(21) Appl. No.: 17/120,498

(22) Filed: Dec. 14, 2020

(65) Prior Publication Data

US 2021/0187267 A1    Jun. 24, 2021

Related U.S. Application Data

(60) Provisional application No. 62/952,838, filed on Dec. 23, 2019.

(51) Int. Cl.
*A61M 39/16* (2006.01)
*A61L 2/18* (2006.01)
*A61M 39/20* (2006.01)

(52) U.S. Cl.
CPC ............. *A61M 39/162* (2013.01); *A61L 2/18* (2013.01); *A61M 39/20* (2013.01)

(58) Field of Classification Search
CPC ........ A61M 39/162; A61M 39/20; A61L 2/18
See application file for complete search history.

(56) References Cited

U.S. PATENT DOCUMENTS

| 3,403,679 A | 10/1968 | Sinclair et al. |
|---|---|---|
| 4,417,890 A | 11/1983 | Dennehey et al. |
| 4,597,758 A | 7/1986 | Aalto et al. |
| 4,642,102 A | 2/1987 | Ohmori |
| 4,711,363 A | 12/1987 | Marino |

(Continued)

FOREIGN PATENT DOCUMENTS

| CA | 2523133 C | 2/2013 |
|---|---|---|
| CN | 1322119 A | 11/2001 |

(Continued)

OTHER PUBLICATIONS

"PCT International Search Report and Written Opinion in PCT/US2021/027219 dated Oct. 22, 2021, 22 pages".

(Continued)

*Primary Examiner* — Bradley J Osinski
(74) *Attorney, Agent, or Firm* — Servilla Whitney LLC

(57) ABSTRACT

A disinfecting cap is described including a housing, a protrusion and a cap cover, the housing including a top wall, an essentially cylindrical sidewall forming a first cavity, and an open bottom end opposite the top wall formed by the cylindrical sidewall with an opening to the first cavity within the housing for receiving a hub of a female needleless connector or a male needleless connector, wherein the protrusion is positioned within the first cavity and includes an inner surface, an outer surface and an end distal the top wall of the housing, the inner surface of the protrusion defining a second cavity, and wherein the outer surface of the protrusion and an inner surface of the essentially cylindrical sidewall define a gap therebetween, and the cap cover is dimensioned and positioned to cover at least a portion of the gap between the outer surface of the protrusion and the inner surface of the housing.

25 Claims, 12 Drawing Sheets

(56) References Cited

U.S. PATENT DOCUMENTS

| | | |
|---|---|---|
| 4,738,376 A | 4/1988 | Markus |
| 4,906,231 A | 3/1990 | Young |
| 5,084,017 A | 1/1992 | Maffetone |
| 5,496,288 A | 3/1996 | Sweeny |
| 5,676,406 A | 10/1997 | Simmons et al. |
| 5,755,696 A | 5/1998 | Caizza |
| 5,984,123 A | 11/1999 | Mogami et al. |
| 6,565,529 B1 | 5/2003 | Kimber et al. |
| 6,632,199 B1 | 10/2003 | Tucker et al. |
| 7,083,605 B2 | 8/2006 | Miyahara |
| 8,012,131 B2 | 9/2011 | Moser et al. |
| 8,388,894 B2 | 3/2013 | Colantonio |
| 8,647,308 B2 | 2/2014 | Solomon et al. |
| 8,721,627 B2 | 5/2014 | Alpert |
| 8,777,504 B2 | 7/2014 | Shaw et al. |
| 8,961,475 B2 | 2/2015 | Solomon et al. |
| 9,039,989 B2 * | 5/2015 | Liu ............... A61L 2/16 422/300 |
| 9,132,223 B1 | 9/2015 | Wakeel |
| 9,192,449 B2 | 11/2015 | Kerr et al. |
| 10,166,381 B2 | 1/2019 | Gardner et al. |
| 10,376,686 B2 | 8/2019 | Burkholz et al. |
| 10,589,080 B2 | 3/2020 | Hitchcock et al. |
| 10,603,481 B2 | 3/2020 | Avula et al. |
| 10,871,246 B2 | 12/2020 | Marici et al. |
| 11,353,147 B2 | 6/2022 | Marici |
| 11,511,100 B2 | 11/2022 | Ryan |
| 11,628,288 B1 | 4/2023 | Solomon et al. |
| 2003/0093009 A1 | 5/2003 | Newby et al. |
| 2003/0209681 A1 | 11/2003 | Leinsing et al. |
| 2004/0039341 A1 | 2/2004 | Ranalletta |
| 2004/0044318 A1 | 3/2004 | Fiser et al. |
| 2005/0147525 A1 | 7/2005 | Bousquet |
| 2005/0197646 A1 | 9/2005 | Connell et al. |
| 2007/0060904 A1 | 3/2007 | Vedrine et al. |
| 2008/0010766 A1 | 1/2008 | Kaufman et al. |
| 2008/0171995 A1 | 7/2008 | Mtullo et al. |
| 2008/0177250 A1 | 7/2008 | Howlett et al. |
| 2010/0000040 A1 | 1/2010 | Shaw et al. |
| 2010/0049170 A1 | 2/2010 | Solomon et al. |
| 2010/0050351 A1 | 3/2010 | Colantonio et al. |
| 2010/0100056 A1 | 4/2010 | Cawthon et al. |
| 2011/0046603 A1 | 2/2011 | Felsovalyi et al. |
| 2011/0054440 A1 | 3/2011 | Lewis |
| 2011/0213341 A1 | 9/2011 | Solomon et al. |
| 2011/0264037 A1 | 10/2011 | Foshee et al. |
| 2012/0039764 A1 | 2/2012 | Solomon et al. |
| 2012/0111368 A1 | 5/2012 | Rahimy et al. |
| 2012/0123386 A1 | 5/2012 | Tsals |
| 2012/0302997 A1 | 11/2012 | Gardner et al. |
| 2013/0085474 A1 | 4/2013 | Charles et al. |
| 2013/0171030 A1 | 7/2013 | Ferlic et al. |
| 2013/0197485 A1 | 8/2013 | Gardner et al. |
| 2013/0338644 A1 | 12/2013 | Solomon et al. |
| 2014/0052074 A1 | 2/2014 | Tekeste |
| 2014/0150832 A1 | 6/2014 | Rogers et al. |
| 2015/0094666 A1 | 4/2015 | Bates et al. |
| 2016/0045629 A1 | 2/2016 | Gardner et al. |
| 2016/0067422 A1 | 3/2016 | Davis et al. |
| 2016/0158520 A1 | 6/2016 | Ma et al. |
| 2017/0203087 A1 | 7/2017 | Ryan et al. |
| 2018/0085568 A1 * | 3/2018 | Drmanovic ......... A61M 5/3134 |
| 2018/0200500 A1 | 7/2018 | Ziebol et al. |
| 2018/0237190 A1 | 8/2018 | Iwasaki |
| 2018/0243547 A1 | 8/2018 | Fox et al. |
| 2018/0256879 A1 | 9/2018 | Chiu et al. |
| 2018/0256883 A1 | 9/2018 | Follman et al. |
| 2019/0151643 A1 | 5/2019 | Alpert |
| 2019/0234540 A1 | 8/2019 | Marici |
| 2019/0308006 A1 | 10/2019 | Erekovcanski et al. |
| 2019/0351212 A1 | 11/2019 | Dudar et al. |
| 2020/0238070 A1 | 7/2020 | Ryan |
| 2021/0100996 A1 | 4/2021 | Wijesuriya et al. |
| 2021/0187267 A1 | 6/2021 | Jiang |
| 2022/0273931 A1 | 9/2022 | Jiang et al. |
| 2023/0080687 A1 | 3/2023 | Ryan |

FOREIGN PATENT DOCUMENTS

| | | |
|---|---|---|
| CN | 101631585 A | 1/2010 |
| CN | 101980746 A | 2/2011 |
| CN | 201807018 U | 4/2011 |
| CN | 102188766 A | 9/2011 |
| CN | 102448502 A | 5/2012 |
| CN | 103025374 A | 4/2013 |
| CN | 103083767 A | 5/2013 |
| CN | 204161736 U | 2/2015 |
| CN | 206198472 U | 5/2017 |
| DE | 20017013 U1 | 12/2000 |
| DE | 10247963 A1 | 5/2004 |
| DE | 202005004079 U1 | 7/2006 |
| EP | 0589379 A1 | 3/1994 |
| EP | 2832391 A1 | 2/2015 |
| GB | 2408259 A | 5/2005 |
| JP | H03139363 A | 6/1991 |
| JP | H04501672 A | 3/1992 |
| JP | 2001502191 A | 2/2001 |
| JP | 2001521792 A | 11/2001 |
| JP | 2004208740 A | 7/2004 |
| JP | 2008532701 A | 8/2008 |
| JP | 2008239164 A | 10/2008 |
| JP | 2010527276 A | 8/2010 |
| JP | 2015517377 A | 6/2015 |
| JP | 2016511119 A | 4/2016 |
| JP | 2016104214 A | 6/2016 |
| WO | 200024442 A1 | 5/2000 |
| WO | 2011066586 A1 | 6/2011 |
| WO | 2013046857 A1 | 4/2013 |
| WO | 2014159346 A1 | 10/2014 |
| WO | 2015127285 A1 | 8/2015 |
| WO | 2015174953 A1 | 11/2015 |
| WO | 2017087400 A1 | 5/2017 |
| WO | 2017095373 A1 | 6/2017 |
| WO | 2018106508 A1 | 6/2018 |
| WO | 2018237090 A1 | 12/2018 |
| WO | 2019212637 A1 | 11/2019 |
| WO | 2020112767 A1 | 6/2020 |

OTHER PUBLICATIONS

"Non-Final Office Action in U.S. Appl. No. 17/076,102 dated Aug. 24, 2021, 10 pages".

PCT Invitation to Pay Additional Fees in PCT/US2021/019546, dated Jun. 15, 2021, 17 pages.

Non-Final Office Action in U.S. Appl. No. 16/378,015, dated Mar. 30, 2021, 10 pages.

PCT International Search Report and Written Opinion in PCT/US2020/065229 dated Mar. 29, 2021, 12 pages.

PCT International Search Report and Written Opinion in PCT/US2021/027214 dated Jul. 19, 2021, 14 pages.

PCT International Search Report and Written Opinion in PCT/US2021/027218 dated Jul. 22, 2021, 14 pages.

PCT International Search Report and Written Opinion in PCT/US2021/027220 dated Jul. 21, 2021, 15 pages.

PCT Invitation to Pay Additional Fees in PCT/US2021/027219, dated Jul. 22, 2021, 15 pages.

PCT International Search Report and Written Opinion in PCT/US2020/057611 dated Feb. 5, 2021, 11 pages.

Final Office Action in U.S. Appl. No. 16/253,683, dated Dec. 23, 2020, 9 pages.

Final Office Action in U.S. Appl. No. 16/254,747, dated Jan. 22, 2021, 15 pages.

* cited by examiner

UNIVERSAL DISINFECTION CAP

CROSS-REFERENCE TO RELATED APPLICATIONS

This application claims priority under 35 U.S.C. § 119(e) to U.S. Provisional Application No. 62/952,838, filed Dec. 23, 2019, the disclosures of which are incorporated herein by reference in their entirety.

TECHNICAL FIELD

The present disclosure generally relates to a device for disinfecting and sterilizing access ports with, e.g., male and female luer fittings, and, in particular, to disinfecting and sterilizing devices capable of accommodating multiple types of connectors. Generally, exemplary embodiments of the present disclosure relate to the field of threaded fitting, including medical caps and medical disinfection caps, and in particular caps and/or disinfection caps with cap covers for use with fluid luer connectors.

BACKGROUND

Vascular access devices (VAD's) are commonly used therapeutic devices and include intravenous (IV) catheters. There are two general classifications of VAD's: peripheral catheters and central venous catheters. Bacteria and other microorganisms may gain entry into a patient's vascular system from access hubs and ports/valves upon connection to the VAD to deliver the fluid or pharmaceutical. Each access hub (or port/valve or connection) is associated with some risk of transmitting a catheter related bloodstream infection (CRBSI), which can be costly and potentially lethal.

In developed markets, when utilizing an IV catheter, a needleless connector will typically be used to close off the system and then subsequently accessed to administer medication or other necessary fluids via the catheter to the patient. INS Standards of Practice recommend the use of a needleless connector and state that it should be "consistently and thoroughly disinfected using alcohol, tincture of iodine or chlorhexidine gluconate/alcohol combination prior to each access." The disinfection of the needleless connector is ultimately intended to aid in the reduction of bacteria that could be living on the surface and possibly lead to a variety of catheter related complications including CRBSI. Nurses will typically utilize a 70% isopropyl alcohol (IPA) pad to complete this disinfection task by doing what is known as "scrubbing the hub." However, compliance to this practice is typically very low. In addition to a lack of compliance to "scrubbing the hub", it has also been noted through clinician interviews that there is often a variation in scrub time, dry time and the number of times the needleless connector is scrubbed.

Throughout the sequence of procedures associated with the transmission of a microorganism that can cause a CRBSI, there are many risks of contact or contamination. Contamination can occur during drug mixing, attachment of a cannula, and insertion into the access hub. Because the procedure to connect to a VAD is so common and simple, the risk associated with entry into a patient's vascular system has often been overlooked. Presently, the risk to hospitals and patients is a substantial function of the diligence of the clinician performing the connection, and this diligence is largely uncontrollable.

In order to decrease CRBSI cases and to ensure VAD's are used and maintained correctly, standards of practice have been developed, which include disinfecting and cleaning procedures. Disinfection caps have been added to the Society for Healthcare Epidemiology of America (SHEA) guidelines. Currently, caps for male needleless connectors, female needleless connectors, intravenous (IV), and hemodialysis lines may be susceptible to microbe and/or other contaminant ingress. Thus, there is a need for a cap cover that protects disinfection caps from microbe and/or other contaminant ingress.

SUMMARY

A first aspect of the present disclosure relates to a cap including a housing, a protrusion and a cap cover.

The housing can include a top wall, an essentially cylindrical sidewall forming a first cavity, and an open bottom end opposite the top wall formed by the cylindrical sidewall with an opening to the first cavity within the housing for receiving a hub of a female needleless connector or a male needleless connector. The protrusion is positioned within the first cavity and may be integrally formed with the housing or be a removable insert. The protrusion may include a sidewall having an inner surface and an outer surface, the inner surface of the protrusion defining a second cavity and the outer surface facing an inner surface of the essentially cylindrical sidewall of the housing. An inner thread can be included on the inner surface of the protrusion, the inner thread being sufficient to interlock with a mating feature of the female needleless connector. An outer thread can be included on the outer surface of the protrusion, the outer thread being sufficient to interlock with a mating feature of the male needleless connector. In one or more embodiments, the protrusion sidewall includes at least one gap. The sidewall may define one or more prongs separated by one or more respective gaps. In one or more embodiments, at least one of the prongs can be configured to bend to facilitate interference fit between the protrusion and the mating feature of the male needleless connector or female needleless connector. In one or more embodiments, the protrusion can extend essentially from an inner surface of the top wall toward the opposite bottom end of the housing. In one or more embodiments, the protrusion can extend essentially parallel to the sidewall of the housing. The outer surface of the protrusion and the inner surface of the housing define a gap therebetween which may be essentially annular.

The cap cover is dimensioned and positioned to cover at least a portion of the gap between the outer surface of the protrusion and the inner surface of the housing. The cap cover may be any suitable shape, such as but not limited to annular and include a top surface, an opposite bottom surface, an exterior wall and an interior wall defining an opening. The cap cover is positioned between the inner surface of the essentially cylindrical sidewall proximal the open bottom end of the housing and the protrusion outer surface, covering at least a portion of the annular gap. In one embodiment at least a portion of the exterior wall of the cap cover is coupled or directly coupled to the inner surface of the housing and the cap cover interior wall is positioned proximal to, adjacent to, directly adjacent to, or abuts the protrusion. The cap cover interior wall may extend to or over an end of the protrusion. In other embodiments at least a portion of the interior wall is coupled or directly coupled to the protrusion end and/or outer surface and the cap cover exterior wall is positioned proximal to, adjacent to, directly adjacent to, or abuts the inner surface of the housing. In either case, the cap cover is free at one edge to deflect downward into the gap upon insertion of a male connector into the cap.

The cap cover may be formed of a resilient material such as but not limited to a polymeric or elastomeric material. The cap cover is flexible enough to be deflected when a male connector is attached to the cap. Upon detachment of the male connector from the cap, the cap cover returns to its original position. When a female connector is used, the gap remains covered by the cap cover and prevents material such as grit, saliva, etc. from entering contaminating the cap and/or creating an obstruction which could prevent coupling the cap to a connector.

The cap cover may form a part of the housing through 2-shot molding or bonded to the housing through lamination, welding, heat adhesive, adhesive or other bonding method.

The cap cover may be made of any suitable material such as but not limited to polymer, elastomer, etc. The thickness of the cap cover may range from 0.1 mm to 3 mm. In some embodiments the thickness of the cap cover is from 0.1 mm to 2 mm.

In embodiments in which the protrusion is or includes a removable insert positioned within the first cavity, the removable insert can include a distal end comprising a distal wall, an open proximal end, and a sidewall extending proximally from the distal wall toward the open proximal end. The sidewall can include a split-thread protrusion integrally formed with the distal wall, the split-thread protrusion having an inner surface and an outer surface. The inner surface of the split-thread protrusion defines a second cavity. An inner thread can be included on the inner surface of the split-thread protrusion, the inner thread being sufficient to interlock with a mating feature of the female needleless connector. An outer thread can be included on the outer surface of the split-thread protrusion, the outer thread being sufficient to interlock with a mating feature of the male needleless connector.

In one or more embodiments, the split-thread protrusion can include one or more cantilevered prongs separated by one or more respective gaps, in which at least one of the prongs is configured to bend to facilitate interference fit between the protrusion and the mating feature of the male needleless connector or female needleless connector.

In one or more embodiments, the sidewall of the insert includes an upper portion and a lower portion. In one or more embodiments, the upper portion of the sidewall can be tapered outward toward the distal wall and the lower portion of the sidewall can be cylindrical.

In accordance with one or more embodiments the protrusion includes an absorbent material including a disinfectant or an antimicrobial agent positioned in the second cavity. In one or more embodiments, the disinfectant or antimicrobial agent disinfects an outer surface and an inner surface of the female needleless connector or male needleless connector when a portion of the female needleless connector or male needleless connector is inserted into the second cavity.

In accordance with still further embodiments, the cap includes a septum coupled to the open bottom end of the housing thereby forming a seal for maintaining the disinfectant or an antimicrobial agent within the second cavity prior to use of the cap.

In one or more embodiments, the cap can include a removable peel seal covering the opening to the second cavity to seal the absorbent material within the second cavity prior to use of the cap.

In one or more embodiments, the absorbent material can be a non-woven or woven material. In one or more embodiments, the absorbent material can be a foam or a sponge. In one embodiment, the foam can be a polyurethane foam. In one or more embodiments, the absorbent material can include slits. In one or more embodiments, a compression of the absorbent material toward the top wall of the housing occurs upon connection to the female needleless connector, whereby compression of the absorbent material disinfects the female needleless connector. In one or more embodiments, the absorbent material can be under radial compression by the inner thread on the inner surface of the split-thread protrusion to retain the absorbent material in the second cavity.

In one or more embodiments, an exterior wall surface of the sidewall of the housing includes a plurality of grip members.

In one or more embodiments, when a hub of the female needleless connector is received within the second cavity, the hub is secured within the second cavity by interlocking at least a portion of the inner thread with a mating feature on the hub of the female needleless connector and the cap cover remains in an undeflected state. In one or more embodiments, when a hub of the male needleless connector is received within the second cavity, the cap cover is deflected in the direction of the housing top wall when a collar of the male needleless connector is received within the gap formed between the protrusion outer wall and inner surface of the housing sidewall and the hub is secured within the first cavity by interlocking at least a portion of the outer thread on the outer surface of the protrusion with a mating feature on a collar of the male needleless connector.

In one or more embodiments, the second cavity can extend further into the housing toward the top wall than the portion of the first cavity defined by the gap formed between the protrusion outer wall and inner surface of the housing sidewall. In one or more embodiments, the profile of the inner thread can be essentially parallel to, or coincide with, a profile of the outer thread.

In one or more embodiments, the inner thread and outer thread can include an inclined thread pattern. In one or more embodiments, the inner thread and outer thread can include a helical-shaped thread pattern. In one or more embodiments, the inner thread or the outer thread can include one or more gaps in the thread pattern.

In one or more embodiments, the inner surface of the protrusion can be essentially parallel to the outer surface of the protrusion.

In one or more embodiments, the disinfectant or the antimicrobial agent can be selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In one or more specific embodiments, the disinfectant or antimicrobial agent includes at least one of chlorhexidine gluconate and chlorhexidine diacetate.

In a still further embodiment an assembly is disclosed including the cap of one or more embodiments herein connected to a medical connector. In one or more embodiments, the medical connector is selected from a male luer connector, a female luer connector, and needleless connector.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

BRIEF DESCRIPTION OF THE DRAWINGS

To assist those of skill in the art in making and using the disclosed energy packet switch and associated systems and methods, reference is made to the accompanying figures, wherein.

DETAILED DESCRIPTION

Figure 1:
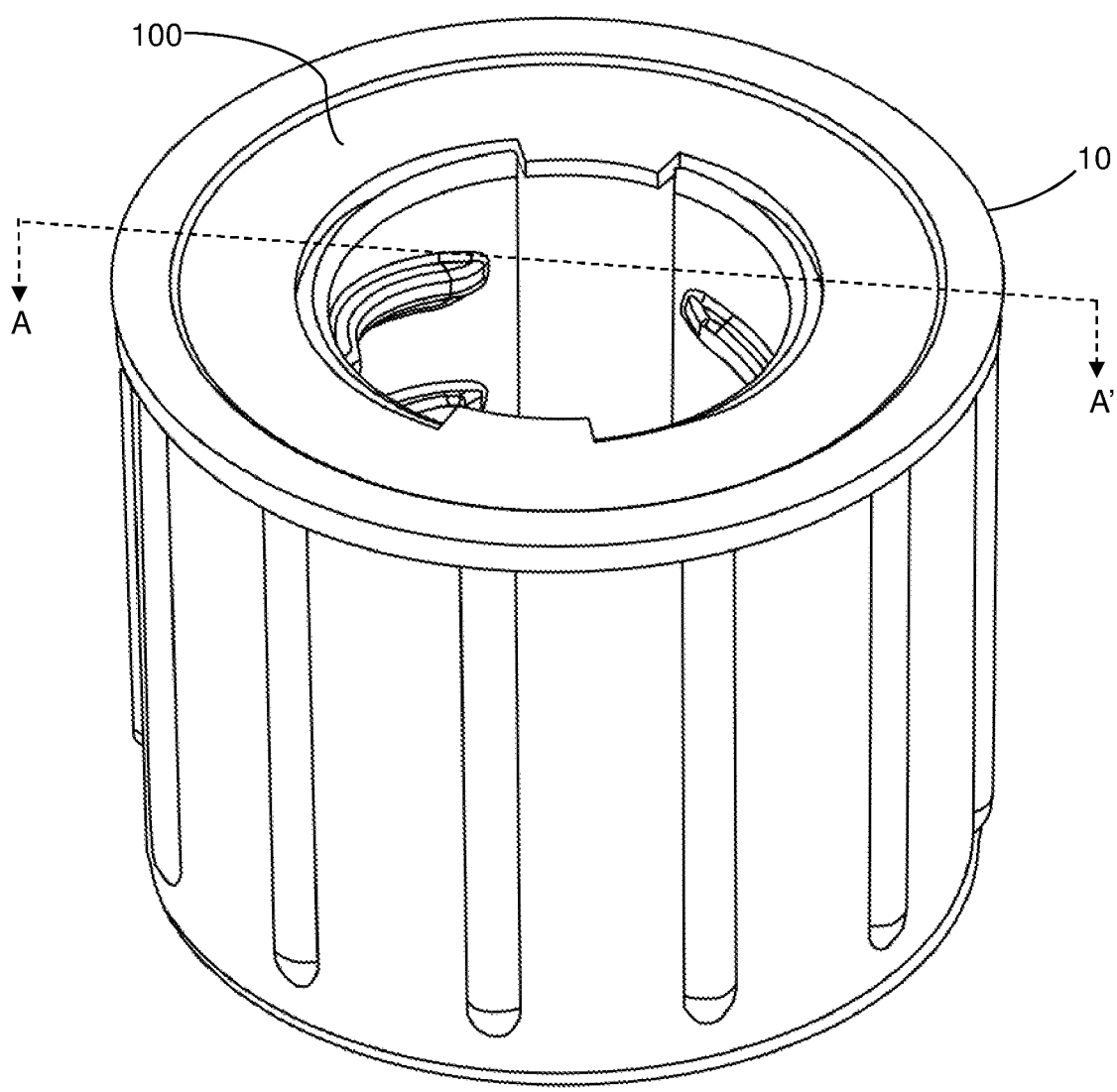
FIG. 1 is an elevated perspective view of a disinfecting cap with a cap cover in accordance with one or more embodiments disclosed herein.
Figure 2:
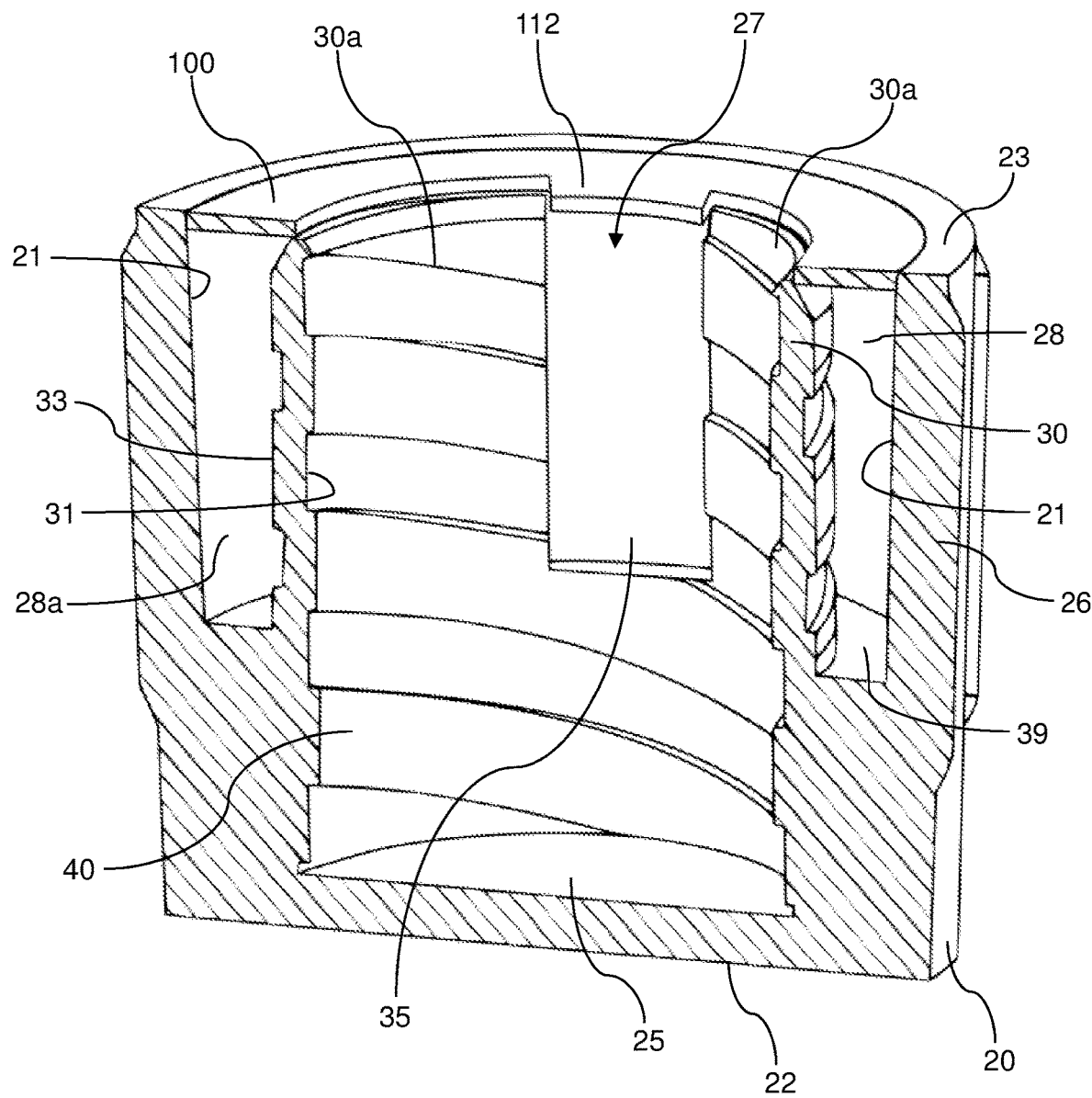
FIG. 2 is a cross-sectional view of the disinfecting cap of FIG. 1 taken along line A-A' in accordance with one or more embodiments disclosed herein.

Before describing several exemplary embodiments of the disclosure, it is to be understood that the disclosure is not limited to the details of construction or process steps set forth in the following description. The disclosure is capable of other embodiments and of being practiced or being carried out in various ways.

With respect to terms used in this disclosure, the following definitions are provided.

As used herein, the use of "a," "an," and "the" includes the singular and plural.

As used herein, the term "catheter related bloodstream infection" or "CRBSI" refers to any infection resulting from the presence of a catheter or IV line.

As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the female end located on the vascular access device (VAD). A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe.

As would be readily appreciated by skilled artisans in the relevant art, while descriptive terms such as "lock", "hole", "tip", "hub", "thread", "sponge", "prong", "protrusion", "tab", "slope", "wall", "top", "side", "bottom" and others are used throughout this specification to facilitate understanding, it is not intended to limit any components that can be used in combinations or individually to implement various aspects of the embodiments of the present disclosure.

It will be understood that when an element is referred to as being "coupled" or "connected" to another element, it can be directly coupled or connected to the other element or intervening elements may also be present. In contrast, when an element is referred to as being "directly coupled" or "directly connected" to another element, there are no intervening elements present. It will be understood that when an element is referred to as being "adjacent" to another element, it can be directly adjacent to the other element or intervening elements may also be present. In contrast, when an element is referred to as being "directly adjacent" to another element, there are no intervening elements present.

Like numbers refer to like elements throughout. As used herein the term "and/or" includes any and all combinations of one or more of the associated listed items.

The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

Embodiments of the disclosure pertain to a universal cap for connection to and disinfection of a medical connector, including male connectors and female connectors, the universal cap having a cap cover positioned and dimensioned to prevent microbial ingress, debris and/other contamination from entering the cap. The male connectors and female connectors can be male luer connectors and female luer connectors. Embodiments of the cap include a housing and a protrusion. The housing includes a sidewall, a closed end and an opposite open end. The sidewall of the housing has a length LC extending from the closed end to the opposite open end defining a chamber. The protrusion, which may be integral with the housing or an insert removably coupled to the housing, extends from the closed end and may be formed concentrically within the housing. The protrusion outer wall and inner surface of the housing sidewall define a gap therebetween. The cap cover is configured and positioned to cover at least a portion of the gap formed between the protrusion outer wall and inner surface of the housing sidewall. In one or more embodiments, the bottom open end includes a peripheral ledge extending radially outward from the open end defining an end face and an engagement surface. The protrusion includes an interior wall surface having one or more threads adapted to engage a female luer connector. The exterior wall surface of the protrusion includes one or more threads that are sized and adapted to receive a male luer connector. The cap may further include absorbent material, a disinfectant and/or antimicrobial agent and a peelable seal and/or septum. The cap provides a mechanical barrier for connectors and contains an antimicrobial agent for disinfection.

Exemplary embodiments of the present disclosure provide caps that can reduce the number of device types and logistics currently needed in the hospital setting for connecting, capping, and/or disinfecting male and female threaded fluid luer connectors, by roughly half by including in a single cap or device features allowing it to be use with both male and female threaded fittings.

In an exemplary implementation of the embodiments of the present disclosure, a cap, connector cap or disinfecting cap includes an integrated thread, or threads, and other features in any and all combinations allowing it to interface with both male and female threaded fittings.

According to further exemplary implementations of the embodiments of the present disclosure, configuration of structural elements making up the cap include one or more cantilevered prongs disposed in the inner cavity of the cap, the cantilevered prongs having an inner thread to connect to female medical connectors and an outer thread to connect to male medical connectors, to facilitate securing of the cap onto a female fitting or onto a male fitting, respectively.

According to yet further exemplary implementations of the embodiments of the present disclosure, both of the male and female threads may coincide with each other on the inner and outer face of the threaded protrusion.

According to still further exemplary implementations of the embodiments of the present disclosure, the cantilevered prong may be in the form of protrusion and may be of a split thread type in which the protrusion may bend in order to allow better interference fit compliance with the fittings.

According to still further exemplary implementations of the embodiments of the present disclosure, female threads are sized and have a thread pattern that will engage with a standard ISO594-2 type of male fitting and/or a male threads that are sized and have a thread pattern that will engage with a standard ISO594-2 type of female fitting. An example of an ISO594-2 type of fitting is a Q-style fitting.

In one or more embodiments, the female connector may be selected from the group consisting essentially of needle-free connectors, catheter luer connectors, stopcocks, and hemodialysis connectors. In one or more embodiments, the needleless connector is selected from a Q-Syte connector, MaxPlus, MaxPlus Clear, MaxZero, UltraSite, Caresite, InVision-Plus, Safeline, OneLink, V-Link, ClearLink, NeutraClear, Clave, MicroClave, MicroClave Clear, Neutron, NanoClave, Kendall, Nexus, InVision, Vadsite, Bionector, etc.

In one or more embodiments, the male connector may be an intravenous tubing end, a stopcock or male lock luer.

Referring now to the drawings, wherein like reference numerals designate identical or corresponding parts throughout the several views, embodiments of the present disclosure are described as follows.

A first aspect of the present disclosure relates to a cap 10 including a housing 20, a protrusion 30 and a cap cover 100. With reference to FIGS. 1-4, housing 20 can include a top wall 22, an essentially cylindrical sidewall 26 forming a first cavity 28, and an open bottom end 23 opposite the top wall 22 formed by the cylindrical sidewall 26, with an opening 27 within the housing 20 for receiving a hub of a female needleless connector or a male needleless connector. In one embodiment, protrusion 30 is integrally formed with the housing 20 and is positioned within the first cavity 28. Protrusion 30 includes a sidewall 32 including an inner surface 31 and an outer surface 33, the inner surface 31 of protrusion 30 defining a second cavity 40, and an end 37 distal from top wall 22.

In one or more embodiments, the cap 10 of the present disclosure has an inner thread 36 having a size and pitch to engage a threadable segment of a female connector, such as for example, a female luer connector. Such connectors are generally and commonly used as catheter and other fluid-tight protective connectors in medical applications. In some embodiments, cap 10 provides a protective cover for a female luer connector when engaged with the connector when threads from the female luer connector engage and form a releasable connection with inner threads 36 of cap 10. An inner thread 36 can be included on the inner surface 31 of protrusion 30, the inner thread 36 being sufficient to interlock with a mating feature of the female needleless connector. An outer thread 38 can be included on the outer surface 33 of protrusion 30, the outer thread 33 being sufficient to interlock with a mating feature of the male needleless connector. In one or more embodiments, the sidewall 32 of protrusion 30 can include one or more prongs 30a separated by one or more respective gaps 35. In one or more embodiments, at least one of the prongs 30a can be configured to bend to facilitate interference fit between the protrusion 30 and a mating feature of the male needleless connector or female needleless connector. In one or more embodiments, protrusion 30 can extend essentially from an inner surface 25 of the top wall 22 toward the bottom end 23 of the housing 20. In one or more embodiments, the protrusion 30 can extend essentially in axial alignment with the sidewall 26 of the housing 20.

In an exemplary implementation of embodiments of the present disclosure, protrusion 30 can be cantilevered, for example by having one or more gaps or cutouts 35. In an exemplary implementation, at least a portion of the a cantilevered protrusion 30 may bend in order to allow better interference fit compliance with the fitting such as at least one of male connector or female connector.

In still further exemplary implementation, protrusion 30 can extend essentially parallel to sidewall 26.

In yet a further exemplary implementation, cavity 40 can extend further into the cap 10 toward inner surface 25 of top wall 22 than the portion of the first cavity 28 defined by the gap 28a terminating at top surface 39.

In still yet further exemplary implementation, a profile of the inner thread 36 and/or the inner surface 31 can essentially parallel, or coincide with, a profile of the outer thread 38 and/or the outer surface 33, respectively.

The outer surface 33 of the protrusion 30 and an inner surface 21 of the housing 20 define a gap 28a therebetween. The gap 28a may be annular. A cap cover 100 is positioned between the inner surface 21 of the sidewall 26 proximal the bottom end 23 of the housing and the protrusion outer surface 33, covering at least a portion of the annular gap 28a. The cap cover 100 includes an annular body 102, which includes an interior wall 104 defining an opening 114 in the annular body 102, an exterior wall 106, a top surface 108 and an opposing bottom surface 110. The thickness and composition of the cap cover 100 are optimally suited to provide the most sufficient coverage of the gap 28a and to allow sufficient flexion of the cap cover 100 to be used with male connectors. In one embodiment at least a portion of the exterior wall 106 of the cap cover 100 is coupled or directly coupled to the inner surface 21 of the housing and the cap cover interior wall 104 is positioned proximal to, adjacent or directly adjacent to, or abuts the protrusion outer surface 33. The cap cover interior wall 104 may extend to or over the end 37 of the protrusion. In other embodiments at least a portion of the interior wall 104 is coupled or directly coupled to the protrusion end 37 and/or outer surface 33. In other embodiments at least a portion of the interior wall 104 is directly coupled to the protrusion end 37 and/or outer surface 33 and the cap cover exterior wall 106 is positioned proximal to, adjacent to, directly adjacent to or abuts the inner surface 21 of the housing 20.

In at least one embodiment the cap cover 100 includes tabs 112 extending into the opening 114. The tabs 112 may be configured and oriented to cover openings formed by gaps 35 of protrusion 30.

In one or more embodiments, a seal 60 in the form of a peel seal or septum can be provided to seal the opening 27 prior to use of cap 10, for example, by attachment to a surface of a rim 29 of an open bottom 23 of housing 20, as described for example in U.S. patent application Ser. No. 16/261,761 filed Jan. 30, 2019, the entirety of which is incorporated by reference herein. In one or more embodiments, the seal 60 may be disposed over the open bottom 23 of housing 20 to prevent any disinfectant or antimicrobial agent contained therein from exiting the cavity 28.

The seal 60 may be secured to the engagement surface of open bottom end 23 of housing 20. The seal 60 minimizes entry of potential particulate hazard and also provides a substantially impermeable enclosure for the cap 10, provides a leak prevention and protection enclosure, protects the contents of an absorbent material 50 contained within the cavity 40, and/or maintains a sealed, sterilized environment. The seal 60 provides a sufficient seal at a range of temperatures, pressures, and humidity levels. The seal 60 may be any suitable material such as but not limited to an aluminum or multi-layer polymer film. The seal 60 may be heat-sealed or induction sealed to the open bottom end 23 of the housing 20. In one or more embodiments, the seal 60 comprises a moisture barrier. In one or more embodiment the seal 60 is peelable.

In one or more embodiments the cap 10 includes an absorbent material 50. The absorbent material 50 may be under radial compression by the inner thread 36 on the inner surface 31 of protrusion 30 to retain the absorbent material 50 in the cavity 40. In one or more embodiments, the absorbent material 50 is a nonwoven material, foam, or a sponge. In a specific embodiment, the foam is a polyurethane foam. In a specific embodiment the absorbent material 50 is in the form of a foam plug. In one or more embodiments, the absorbent material 50 includes one or more slits.

In yet another exemplary implementation, a disinfecting member or members, such as an absorbent material 50, is in the form of an IPA soaked sponge and/or sponge. In one or more embodiments, absorbent material 50 can also be formed together as a single cleaning member or separate cleaning member can be provided within cavity 28, for example in the gap 28a of cavity 28.

The cap 10 can achieve disinfection when used on luer connectors by integrating disinfectant or antimicrobial agent in the cavity 40 of the cap 10. The disinfectant or antimicrobial agent can be directly included in the cavity 40 or disinfectant or antimicrobial agent can be absorbed into sponges or foam material that fill the cavities of cap 10. Cap 10 is designed to be compatible in interacting with various disinfectants. In one or more embodiments, the disinfectant or antimicrobial agent may include variations of alcohol or chlorhexidine. In one or more embodiments, the disinfectant or antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent comprises at least one of chlorhexidine gluconate and chlorhexidine diacetate. In one or more embodiments, the disinfectant or antimicrobial agent is a fluid or a gel.

Compression of the absorbent material 50 toward the top wall 22 of housing 20 upon connection to the female luer connector or the male luer connector allows the connector to contact the disinfectant or antimicrobial agent to disinfect the female luer connector or the male luer connector.

Figure 5A:
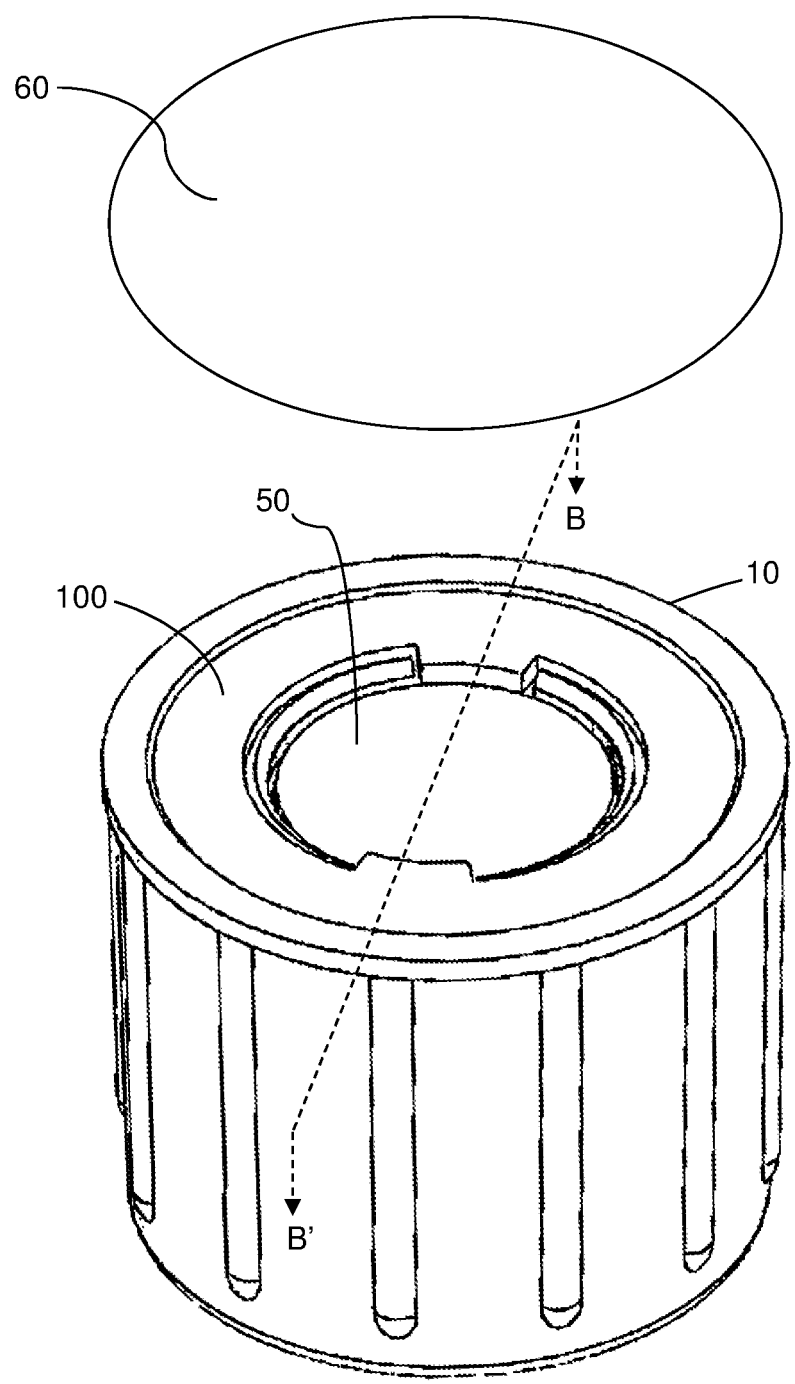
FIG. 5A is an elevated perspective view of a disinfecting cap including an absorbent material in accordance with one or more embodiments disclosed herein.
Figure 5B:
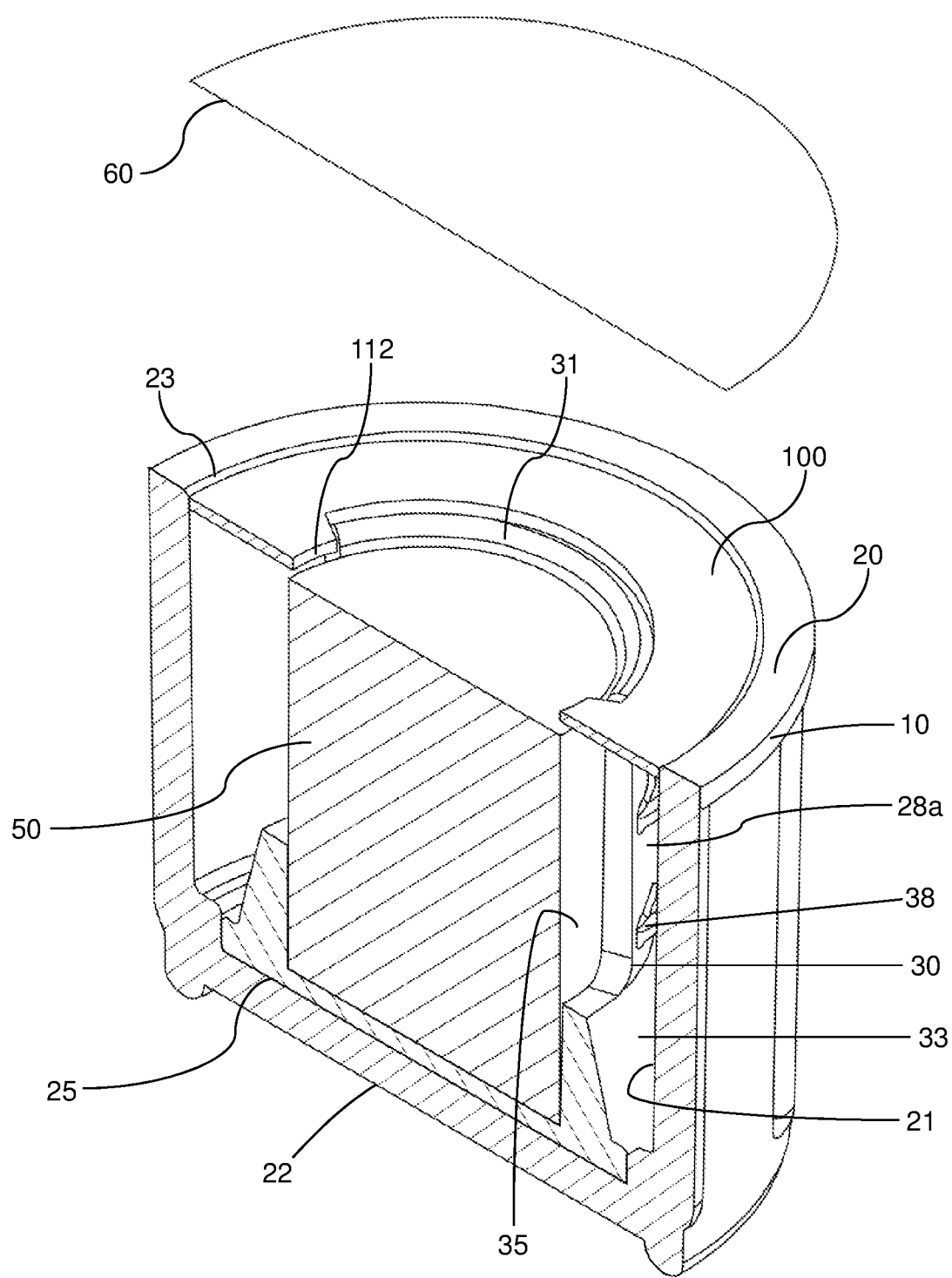
FIG. 5B is a cross-sectional view of the disinfecting cap of FIG. 5A taken along line B-B' in accordance with one or more embodiments disclosed herein.

Referring further to FIGS. 5A and 5B, according to exemplary embodiments of the disclosure, cap 10 can receive a tip or hub 82 of a male needleless connector 80, for example after a seal 60 covering cavity 28 and/or 40 is removed (e.g., wherein the seal 60 is a peel seal) or when the seal 60 is pierced (e.g., wherein the seal 60 is a septum), within cavity 40 and secure the tip or hub 82 of needleless connector 80 within the cavity 40, by securing, for example, threadedly, a collar 84 of connector 80 within gap 28a of cavity 28. At least a portion of exterior wall 106 of the cap cover 100 is anchored to housing 20, while the interior wall 104 is free, so that the cap cover 100 is free to deflect downward into gap 28a toward top surface 39 upon insertion of a male connector 80. One or more threads can be sufficient to interlock with a mating feature (such as one or more protrusions, lugs and/or thread) of collar 84 of needleless connector 80.

Figure 6:
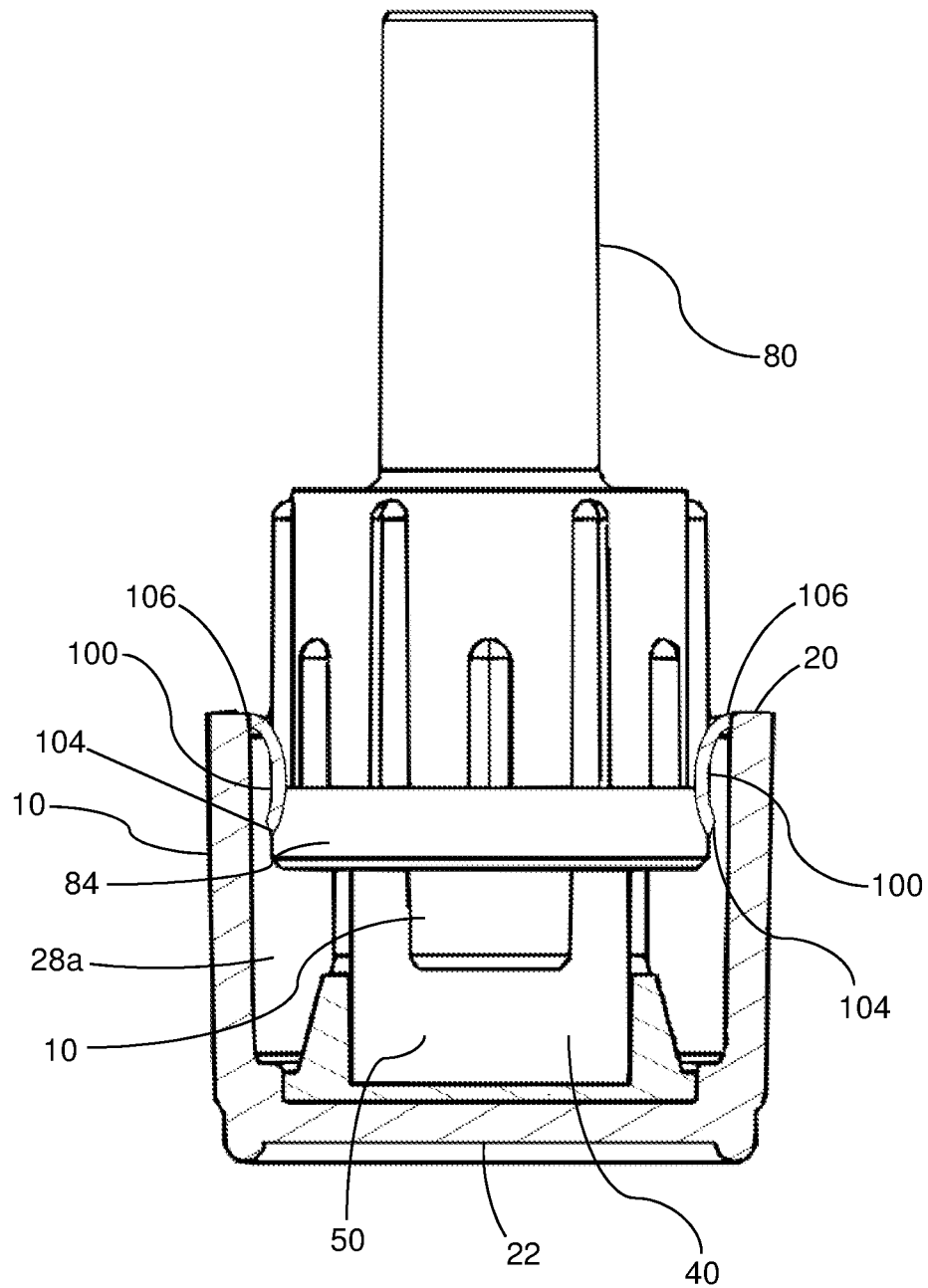
FIG. 6 is a side partial cross-sectional view showing the disinfecting cap of FIG. 5A (cross-sectional view) coupled to a male connector (shown in side view) in accordance with one or more embodiments disclosed herein.
Figure 7:
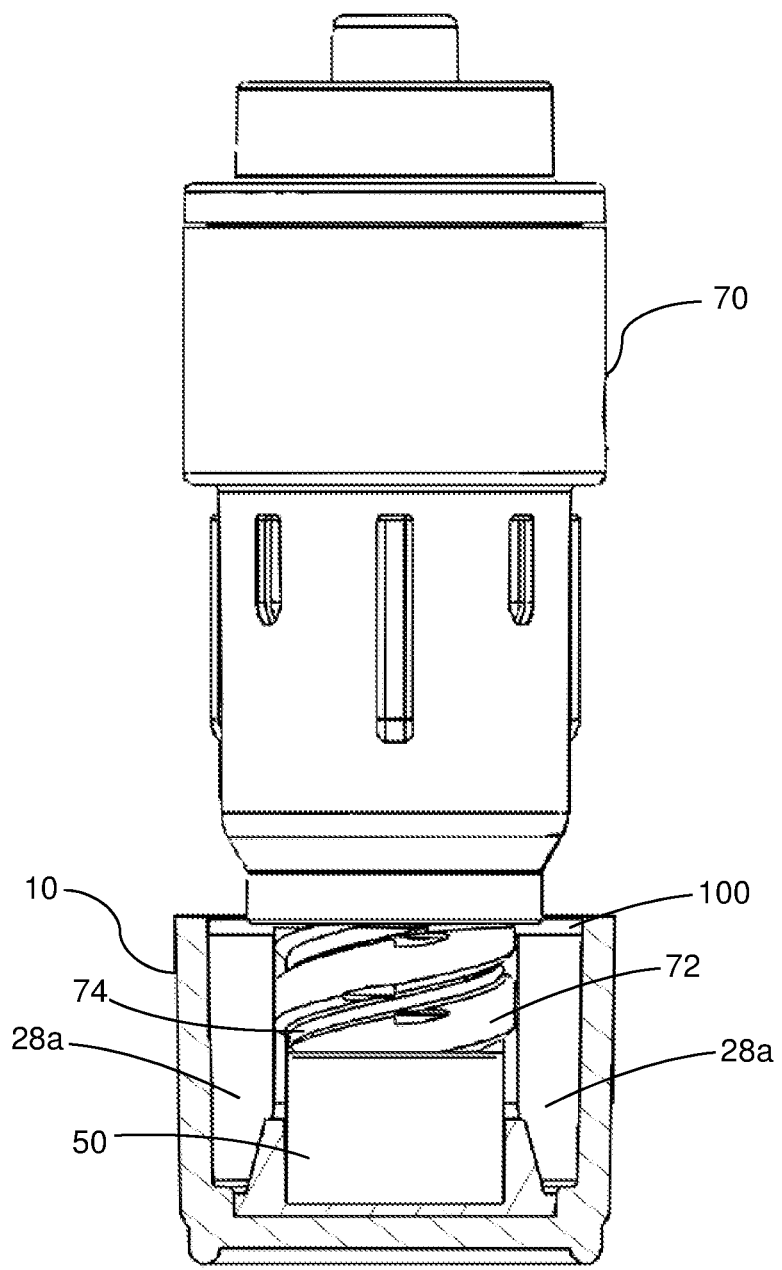
FIG. 7 is a side partial cross-sectional view showing the disinfecting cap of FIG. 5B (cross-sectional view) coupled to a female connector (shown in side view) in accordance with one or more embodiments disclosed herein.

Referring further to FIG. 6, it will be apparent to those skilled in the art based on the present disclosure that the cap 10 can receive a tip or hub 72 of a female needleless connector 70, for example after a seal 60 sealing cavity 28 and/or 40 is removed or pierced, within cavity 40 and secure, for example, threadedly, the tip of needleless connector 70 within cavity 40. One or more threads can be sufficient to interlock with a mating feature 74 (such as one or more protrusions, lugs and/or thread) of a hub or tip 72 of needleless connector 70, as described for example in related U.S. patent application Ser. Nos. 15/408,278 and 15/408,187, both filed on Jan. 17, 2017. In such an embodiment, the cap cover 100 remains undeflected upon coupling of the cap to the female connector 70. The cap cover 100 covers the gap 28a to prevent ingress of contaminants to the gap 28a.

In one or more embodiments the cap cover 100 has sufficient stiffness to be restored to its undeflected position upon removal of the male connector while having sufficient flexibility to deflect.

Figure 8:
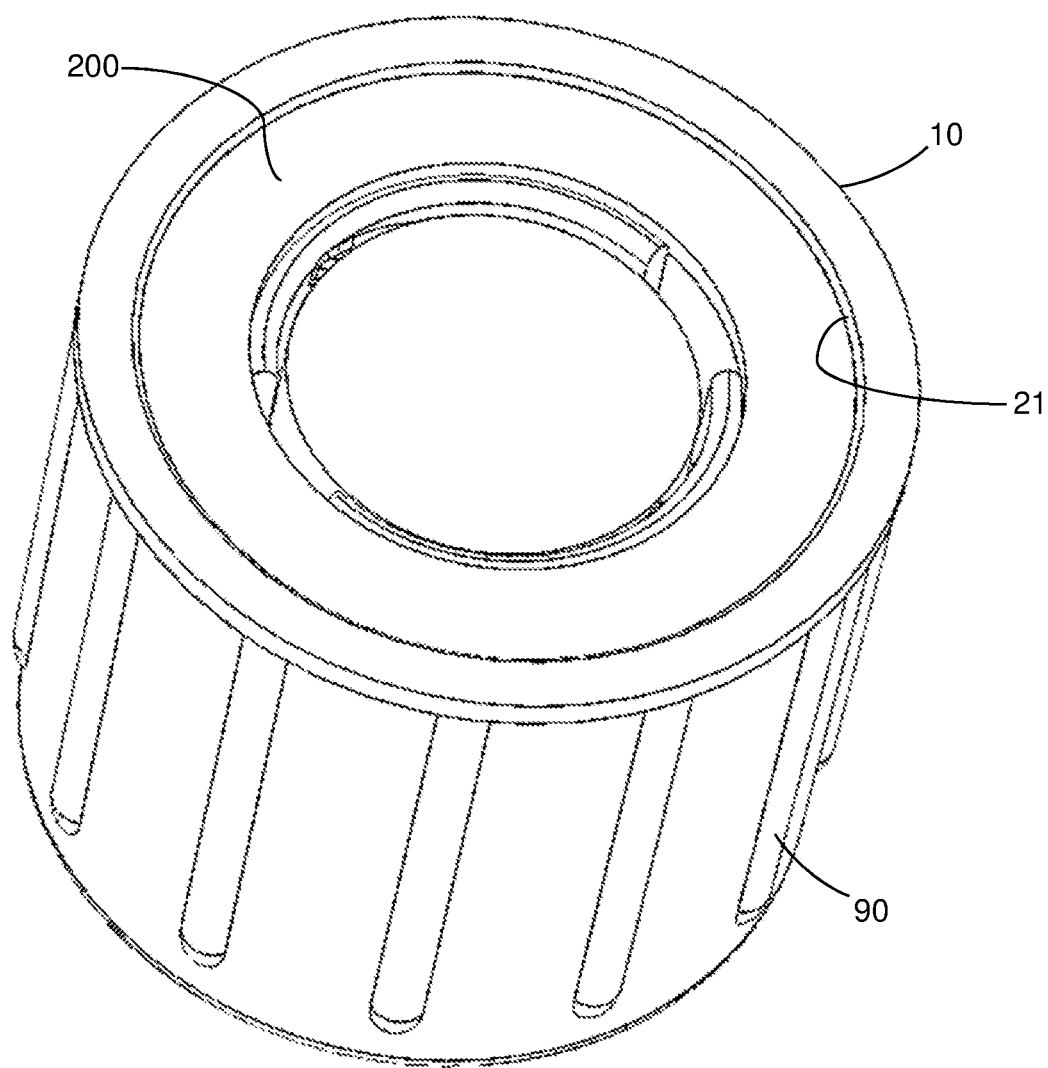
FIG. 8 is an elevated perspective view of a disinfecting cap with a cap cover in accordance with one or more embodiments disclosed herein.
Figure 9:
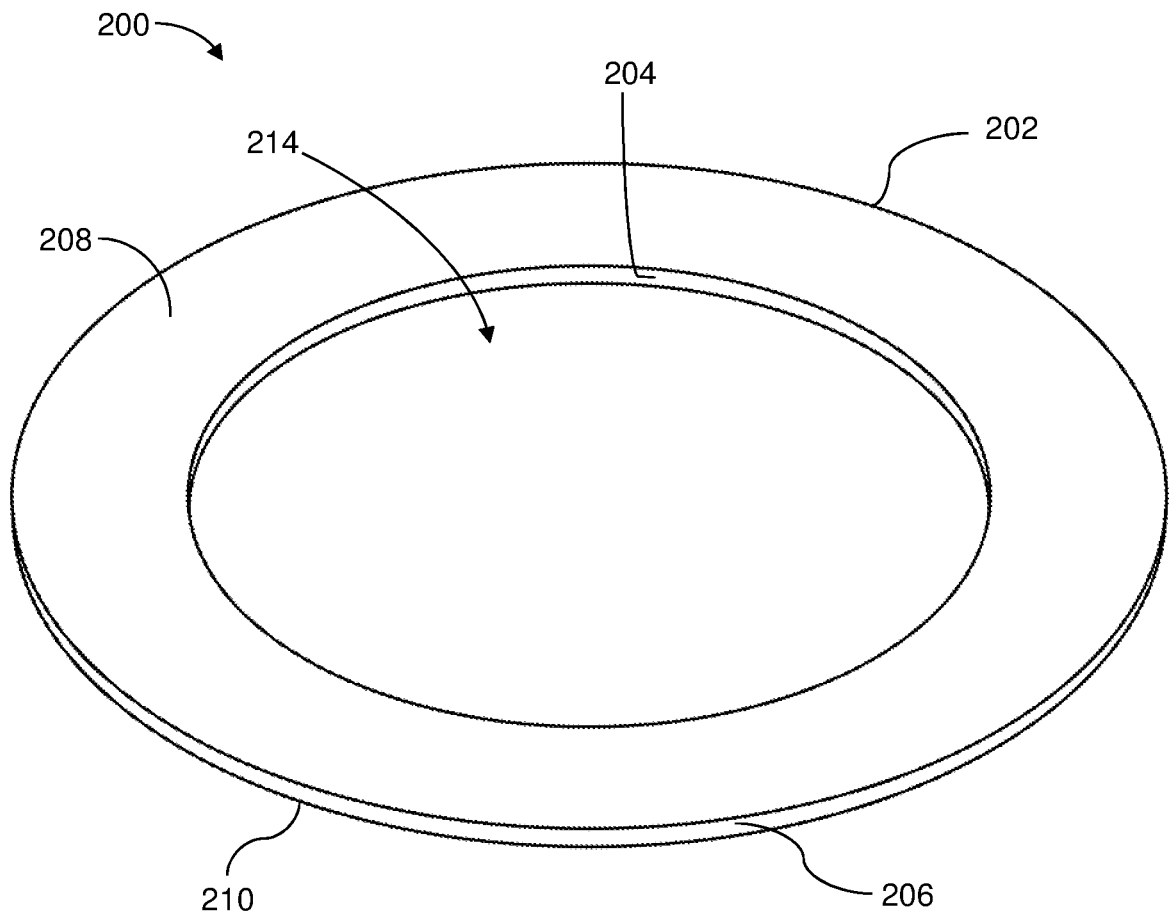
FIG. 9 is an elevated perspective view of a cap cover in accordance with exemplary embodiments of the disclosure.

Now referring to FIGS. 8-11, various embodiments of cap covers are disclosed. With reference to FIGS. 8-9, in one exemplary embodiment a cap 10 includes a cap cover 200 including an annular body 202, which includes an interior wall 204 defining an opening 214 in the annular body 202, an exterior wall 206, a top surface 208 and an opposing bottom surface 210.

Figure 10:
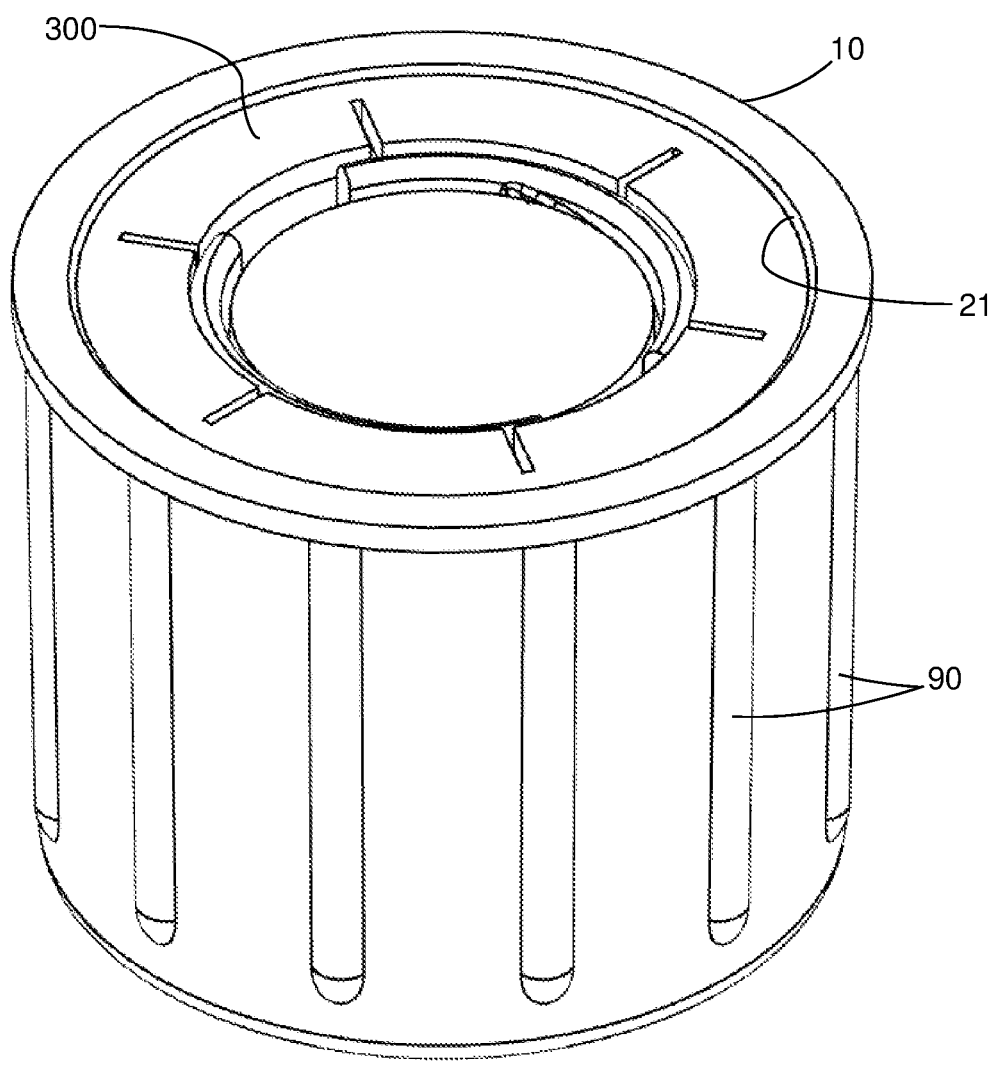
FIG. 10 is an elevated perspective view of a disinfecting cap with a cap cover in accordance with one or more embodiments disclosed herein.
Figure 11:
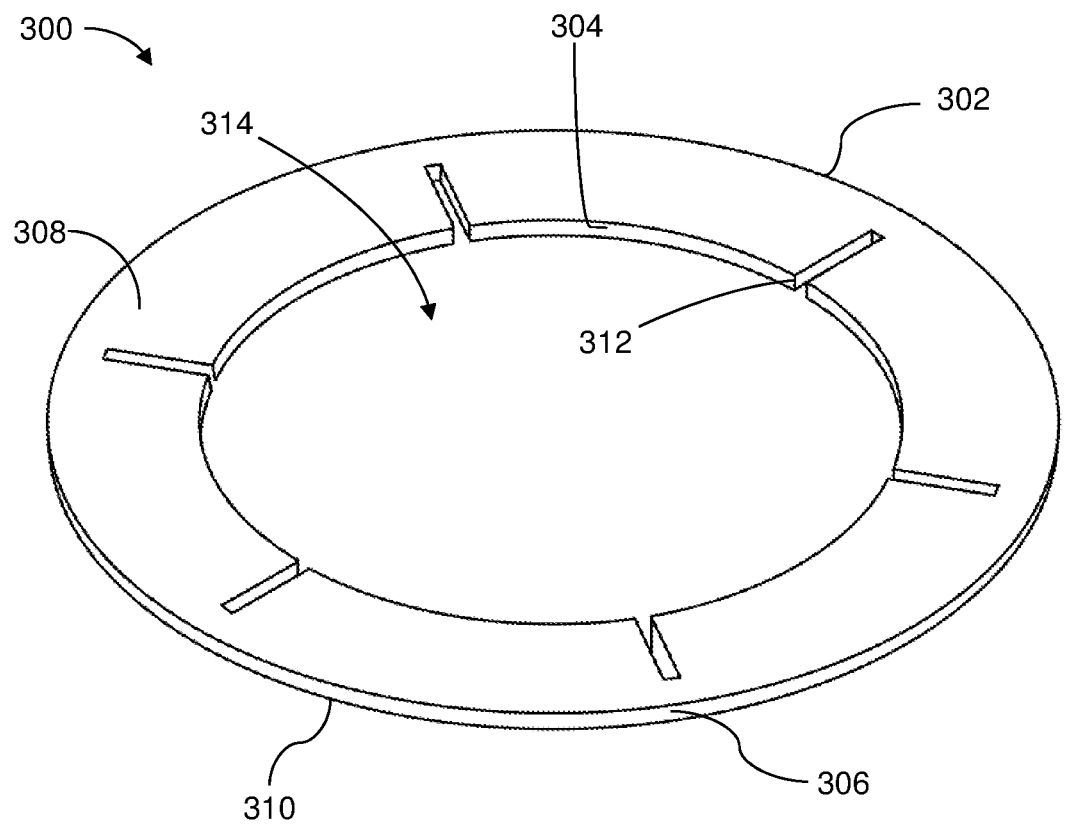
FIG. 11 is an elevated perspective view of a cap cover in accordance with exemplary embodiments of the disclosure.

Now referring to FIGS. 10-11, in a further exemplary embodiment a cap 10 includes a cap cover 300 including an annular body 302, which includes an interior wall 304 defining an opening 314 in the annular body 302, an exterior wall 306, a top surface 308, an opposing bottom surface 310 and a plurality of slits 312 formed in the annular body 302 to facilitate deflection of the cap cover 300 into the gap 28a.

The cap covers 200 and 300 may be positioned in the cap 10 in the same way as described hereinabove with reference to cap cover 100. In some cases it may be more desirable to directly couple the exterior wall 206 or 306 to the inner surface 21 of the sidewall 26 proximal the bottom end 23 of the housing than to directly couple the cap cover interior wall 204 or 304 to the protrusion outer surface 33 or end 37.

The cap covers 100, 200 and 300 disclosed herein may be used in conjunction with any cap having a housing and protrusion in which a gap is formed therebetween. Such caps include but are not limited to those described in U.S. patent application Ser. No. 16/261,761 filed Jan. 30, 2019, the entirety of which is incorporated by reference herein.

In an exemplary implementation of FIGS. 1-4, protrusion 30 is illustrated as comprising two prongs 30a spaced by cutouts 35 and extending essentially from surface 25 of top wall 22. However, also within the scope of the disclosure are caps 10 including a unitary protrusion 30 without any cutouts 35, and caps having a protrusion 30 including any number of identical and/or different (in any dimensional characteristics, such as length width, thickness, or shape) prongs 30a, as long as protrusion 30 is configure to engage a female connector with respect to its inner surface, and engage a male connector with respect to its outer surface.

Figure 3:
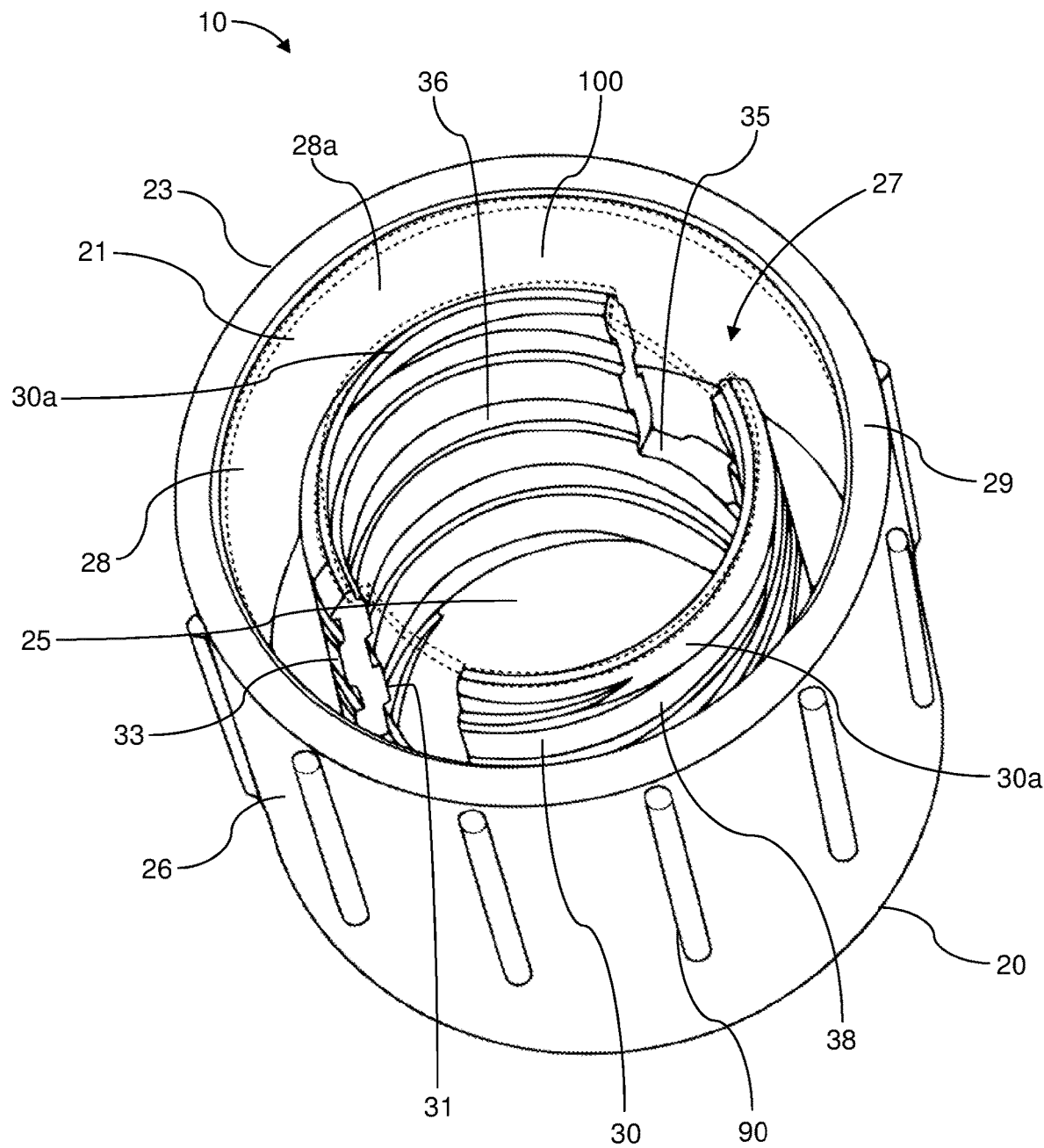
FIG. 3 is an elevated perspective view of a disinfecting cap with a cap cover shown in phantom in accordance with one or more embodiments disclosed herein.
Figure 4:
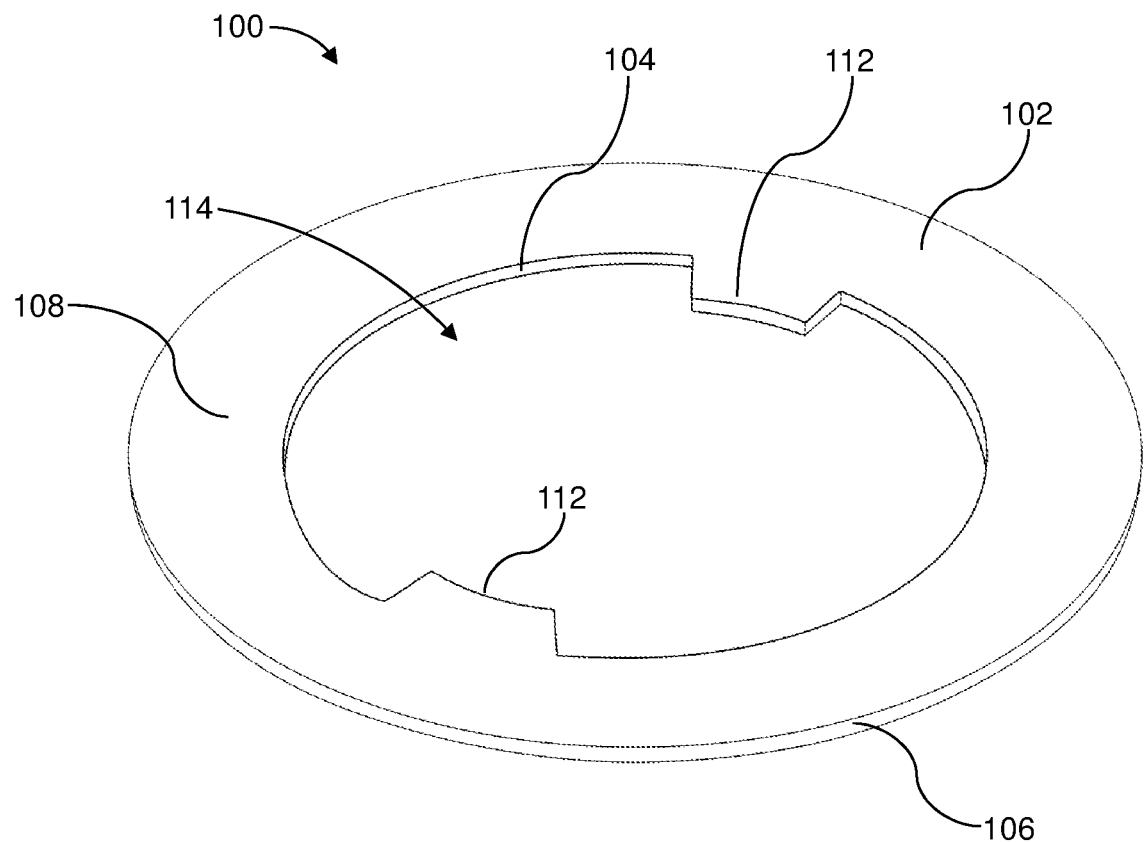
FIG. 4 is an elevated perspective view of a cap cover in accordance with exemplary embodiments of the disclosure.

Referring to FIG. 3, in one or more embodiments, the exterior surface of sidewall 26 may include a plurality of grip members 90.

The cap 10 may be made from any suitable material including but not limited to a number of types of plastic materials such as polycarbonate, polypropylene, polyethylene, polyethylene terephthalate, polylactide, acrylonitrile butadiene styrene or any other moldable plastic material used in medical devices. In one or more embodiments, the cap 10 includes a polypropylene or polyethylene material.

According to exemplary implementations of the embodiments of the disclosure, cap 10 described above can further include an outer housing implementing the safety features and designs described in U.S. patent application No. 62/488,266 filed Apr. 21, 2017 and No. 62/523,506, filed Jun. 22, 2017, for example by modifying walls 22 and/or 26 of housing 20.

According to yet further exemplary implementations of the embodiments of the disclosure, cap 10 described above can be implemented with various venting features and designs described in U.S. patent application Ser. Nos. 15/408,278 and 15/408,187, both filed on Jan. 17, 2017, for example by modifying shape and/or size of protrusion 30, and/or configuration (such as pitch, spacing, thickness, and/or other structural features) of thread 36 and/or thread 38, and/or configuration of surface 31 and/or surface 33.

In another aspect the presently disclosed subject matter relates to an assembly. The assembly includes the cap of one or more embodiments described herein connected to a medical connector. In one or more embodiments, the medical connector is selected from a male luer connector, a female luer connector, and needleless connector.

While the present disclosure has been shown and described with reference to certain exemplary embodiments thereof, it will be understood by those skilled in the art that various changes in form and details may be made therein without departing from the spirit and scope of the embodiments of the present disclosure. For example, a disinfection sponge can comprise any suitable disinfecting or other application-specific substance, and can be made of any suitable material. Also, the inner and/or the outer housing of the cap can be single shot molded, or made by other suitable process. Furthermore, any of the features or elements of any exemplary implementations of the embodiments of the present disclosure as described above and illustrated in the drawing figures can be implemented individually or in any combination(s) as would be readily appreciated by skilled artisans without departing from the spirit and scope of the embodiments of the present disclosure.

In addition, the included drawing figures further describe non-limiting examples of implementations of certain exemplary embodiments of the present disclosure and aid in the description of technology associated therewith. Any specific or relative dimensions or measurements provided in the drawings other as noted above are exemplary and not intended to limit the scope or content of the inventive design or methodology as understood by artisans skilled in the relevant field of invention.

Other objects, advantages and salient features of the disclosure will become apparent to those skilled in the art from the details provided, which, taken in conjunction with the annexed drawing figures, disclose exemplary embodiments of the disclosure.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A disinfecting cap comprising a housing, a protrusion and a cap cover, the housing comprising a top wall, an essentially cylindrical sidewall forming a first cavity, and an open bottom end opposite the top wall formed by the cylindrical sidewall with an opening to the first cavity within the housing for receiving a hub of a female needleless connector or a male needleless connector, wherein the protrusion is positioned within the first cavity and comprises an inner surface, an outer surface and an end distal the top wall of the housing, the inner surface of the protrusion defining a second cavity, and wherein the outer surface of the protrusion and an inner surface of the essentially cylindrical sidewall define a gap therebetween, and the cap cover is dimensioned and positioned to cover at least a portion of the gap between the outer surface of the protrusion and the inner surface of the housing; wherein the cap cover comprises a body comprising a top surface, an opposite bottom surface, an exterior wall and an interior wall defining an opening, and at least a portion of the interior wall is coupled or directly coupled to the protrusion and the cap cover is positioned within the housing such that the cap cover is free to deflect downward into the gap between the outer surface of the protrusion and the inner surface of the housing upon insertion of a male connector into the disinfecting cap.

2. The disinfecting cap of claim 1, wherein the cap cover is annular.

3. The disinfecting cap of claim 1, the cap cover comprising at least one slits formed in the cap cover body.

4. The disinfecting cap of claim 1, wherein the cap cover is positioned between the inner surface of the essentially cylindrical sidewall proximal the open bottom end of the housing and the protrusion.

5. The disinfecting cap of claim 1, wherein at least a portion of the exterior wall of the cap cover is coupled or directly coupled to the inner surface of the housing and the cap cover interior wall is positioned proximal to, adjacent to, directly adjacent to or abuts the outer surface of the protrusion such that the cap cover is free to deflect downward into the gap between the outer surface of the protrusion and the inner surface of the housing upon insertion of a male connector into the disinfecting cap.

6. The disinfecting cap of claim 5, wherein the cap cover interior wall extends to or over the end of the protrusion.

7. The disinfecting cap of claim 1, wherein at least a portion of the interior wall is coupled or directly coupled to the protrusion outer surface and/or protrusion end and the cap cover exterior wall is positioned proximal to, adjacent to, directly adjacent to or abuts the inner surface of the housing.

8. The disinfecting cap of claim 1, the cap cover comprising at least one tab extending into the opening, wherein the at least one tab is configured and oriented to cover at least one gap in the protrusion.

9. The disinfecting cap of claim 1, further comprising a seal disposed over the open bottom end of the housing.

10. The disinfecting cap of claim 1, further comprising an absorbent material positioned in the housing.

11. The disinfecting cap of claim 10, wherein the absorbent material is positioned in the second cavity and comprises a disinfectant or antimicrobial agent.

12. The disinfecting cap of claim 11, wherein the disinfectant or antimicrobial agent is an alcohol or chlorhexidine.

13. The disinfecting cap of claim 11, wherein the disinfectant or antimicrobial agent consists essentially of isopropyl alcohol, ethanol, 2-propanol, butanol, methylparaben, ethylparaben, propylparaben, propyl gallate, butylated hydroxyanisole (BHA), butylated hydroxytoluene, t-butylhydroquinone, chloroxylenol, chlorhexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

14. The disinfecting cap of claim 13, wherein the disinfectant or antimicrobial agent comprises at least one of chlorhexidine gluconate and chlorhexidine diacetate.

15. The disinfecting cap of claim 1, wherein the cap cover comprises a resilient material.

16. The disinfecting cap of claim 1, wherein the cap cover is integral with the housing.

17. The disinfecting cap of claim 1, wherein the thickness of the cap cover is from 0.1 mm to 3 mm.

18. The disinfecting cap of claim 1 wherein the thickness of the cap cover is from 0.1 mm to 2 mm.

19. The disinfecting cap of claim 1, comprising an inner thread on the inner surface of the protrusion, the inner thread being sufficient to interlock with a mating feature of a female needleless connector.

20. The disinfecting cap of claim 1, comprising an outer thread on the outer surface of the protrusion, the outer thread being sufficient to interlock with a mating feature of a male needleless connector.

21. The disinfecting cap of claim 1, wherein the protrusion comprises a sidewall comprising at least one gap and at least one prong.

22. The disinfecting cap of claim 1, wherein the protrusion is integral with the housing.

23. The disinfecting cap of claim 1, wherein the protrusion comprises a removable insert positioned within the first cavity, the removable insert comprising a distal end comprising a distal wall, an open proximal end, and a sidewall extending proximally from the distal wall toward the open proximal end.

24. An assembly comprising the disinfecting cap of claim 1, coupled to a medical connector.

25. The assembly of claim 24, wherein the medical connector is selected from a male luer connector, a female luer connector, and needleless connector.

* * * * *

UNITED STATES PATENT AND TRADEMARK OFFICE
CERTIFICATE OF CORRECTION

PATENT NO. : 11,890,445 B2
APPLICATION NO. : 17/120498
DATED : February 6, 2024
INVENTOR(S) : Chang Jiang et al.

It is certified that error appears in the above-identified patent and that said Letters Patent is hereby corrected as shown below:

On the Title Page

•Page 2, item [56] Line 41, replace "Mtullo" after "7/2008" with "Vitullo".

Signed and Sealed this
Twenty-sixth Day of March, 2024

Katherine Kelly Vidal
*Director of the United States Patent and Trademark Office*